US008304424B2

(12) United States Patent
Leverd et al.

(10) Patent No.: US 8,304,424 B2
(45) Date of Patent: Nov. 6, 2012

(54) FREEZE-DRIED INJECTABLE PHARMACEUTICAL COMBINATION OF SEMISYNTHETIC VINCA ALKALOIDS AND CARBOHYDRATE STABLE AT ROOM TEMPERATURE

(75) Inventors: Elie Leverd, Castres (FR); Joël Bougaret, Francarville (FR); Marie-Dominique Ibarra, Saubens (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 12/514,668

(22) PCT Filed: Dec. 28, 2007

(86) PCT No.: PCT/EP2007/064612
§ 371 (c)(1),
(2), (4) Date: May 13, 2009

(87) PCT Pub. No.: WO2008/080968
PCT Pub. Date: Jul. 10, 2008

(65) Prior Publication Data
US 2010/0087473 A1    Apr. 8, 2010

Related U.S. Application Data

(60) Provisional application No. 60/897,059, filed on Jan. 24, 2007.

(30) Foreign Application Priority Data

Dec. 29, 2006 (FR) ...................... 06 56044

(51) Int. Cl.
*A61K 31/44* (2006.01)
(52) U.S. Cl. ........................ 514/283; 514/281
(58) Field of Classification Search .............. 514/283
See application file for complete search history.

(56) References Cited

U.S. PATENT DOCUMENTS

| 4,619,935 A * | 10/1986 | Robison ........................ 514/281 |
| 4,923,876 A | 5/1990 | Francis et al. |
| 6,127,377 A | 10/2000 | Duflos et al. |
| 6,143,276 A * | 11/2000 | Unger ............................ 424/9.3 |
| 2007/0116753 A1* | 5/2007 | Hong et al. ................... 424/450 |
| 2007/0155768 A1 | 7/2007 | Leverd et al. |

FOREIGN PATENT DOCUMENTS

| EP | 0 392 717 A1 | 10/1990 |
| FR | 2 531 860 A1 | 2/1984 |
| FR | 2 761 990 A1 | 10/1998 |
| FR | 2 863 891 A1 | 6/2005 |
| FR | 2863891 * | 6/2005 |
| WO | WO-03/072082 A1 | 9/2003 |
| WO | WO 03072082 A1 * | 9/2003 |
| WO | WO-2006/099258 A1 | 9/2006 |

OTHER PUBLICATIONS

Brown, M. et al., "Protection of oxygen-sensitive pharmaceuticals with nitrogen", J. Pharm. Sciences, 58(2), 242-245, Feb. 1969.*
Hatley R H M et al., "Stabilization of a pharmaceutical drug substance by freeze-drying: A case study", Drug Stability, Radcliff Medical Prese, Abingdon, GB, vol. 1, No. 2, 1996, pp. 73-85, XP009087829.
Van Drooge D J et al., "Incorporation of Lipophilic Drugs in Sugar Glasses by Lyophilization using a Mixture of Water and Tertiary Butyl Alcohol as Solvent,"Journal of Pharmaceutical Sciences, vol. 93, No. 3, Mar. 2004, pp. 713-725, XP002445775.
Patist A et al., "Preservation mechanisms of trehalose in food and biosystems", Colloids and Surfaces B: Biointerfaces, vol. 40, No. 2, Feb. 10, 2005, pp. 107-113, XP004709042.

* cited by examiner

*Primary Examiner* — Sreeni Padmanabhan
*Assistant Examiner* — Svetlana M Ivanova
(74) *Attorney, Agent, or Firm* — Birch, Stewart, Kolasch & Birch, LLP.

(57) ABSTRACT

This invention relates to pharmaceutical compositions consisting of a semisynthetic derivative of vinca alkaloid, stable at room temperature, in which said derivative is present in the form of a freeze dried product obtained in the presence of at least one carbohydrate.

11 Claims, 1 Drawing Sheet

FREEZE-DRIED INJECTABLE PHARMACEUTICAL COMBINATION OF SEMISYNTHETIC VINCA ALKALOIDS AND CARBOHYDRATE STABLE AT ROOM TEMPERATURE

This application is the National Phase of PCT/EP2007/064612 filed on Dec. 28, 2007, which claims priority under 35 U.S.C. 119(e) to U.S. Provisional Application No. 60/897,059 filed on Jan. 24, 2007, and under 35 U.S.C. 119(a) to Patent Application No. 656044 filed in France on Dec. 29, 2006, all of which are hereby expressly incorporated by reference into the present application.

This invention relates to freeze-dried injectable pharmaceutical compositions of semisynthetic vinca alkaloids that are stable at room temperature.

Generally speaking, the clinical interest of vinca alkaloids has been clearly established for some 40 years. Since then, these compounds have been widely used as anti-cancer agents.

Vinblastine and vincristine were first isolated from the leaves of *Catharanthus roseus* G. Don or *Vinca rosea* L. These alkaloids are dimers consisting of two indole units: catharanthine and vindoline. Vinblastine and vincristine first became available on the market in France in 1963 and 1964 respectively, under the brand names VELBE® and ONCOVIN®. Synthesis studies conducted on vinblastine led to the manufacture of vindesine, the first non-natural derivative and the source of the pharmaceutical preparation ELDISINE (1983).

It is to Poitier et al. that we owe the second non-natural medicinal derivative with a bis indolic structure. This is vinorelbine, a molecule obtained by a semisynthetic route based on the use of catharanthine and vindoline and which has extensive anti-tumour properties. Vinorelbine was registered under the brand name NAVELBINE® for the first time in France in 1989 by Pierre Fabre Medicament for the treatment of non-small cell lung cancer then for the treatment of metastatic cancer of the breast in 1992. An oral form was registered in France in 2001.

These anti-cancer drugs are available in the form of either a ready-to-use solution (ONCOVIN®, NAVELBINE®) or in powder form (VELBE®, ELDISINE®). They must be stored in the refrigerator at a temperature of 2° C. to 8° C. during both transport and storage.

Several years ago, a new family was created by means of chemical reactions in a super-acid medium. A semisynthetic difluorinated derivative, vinflunine, is currently under clinical development.

In the same way as vinorelbine, vinflunine is obtained from anhydrovinblastine which itself results from a biomimetic coupling reaction between catharanthine and vindoline.

For reasons relating to solubility in water, vinflunine is salified in the form of a hydrosoluble salt. For example, ditartrate is isolated after the aqueous solution of this salt is freeze-dried.

Vinflunine ditartrate is a white or practically white powder which must be stored at a negative temperature, below −15° C., under an inert gas atmosphere such as nitrogen or argon. This is also true for vinorelbine ditartrate.

The Applicant's French patent application 2 863 891 ("Vinflunine pharmaceutical composition for parenteral administration, preparation and usage procedure") focuses on the stabilizing effect of dissolving a hydrosoluble salt of vinflunine in an aqueous medium. One of its claims relates to the good stability of the composition for at least 36 months at 5° C.±3° C.

Figure 1:
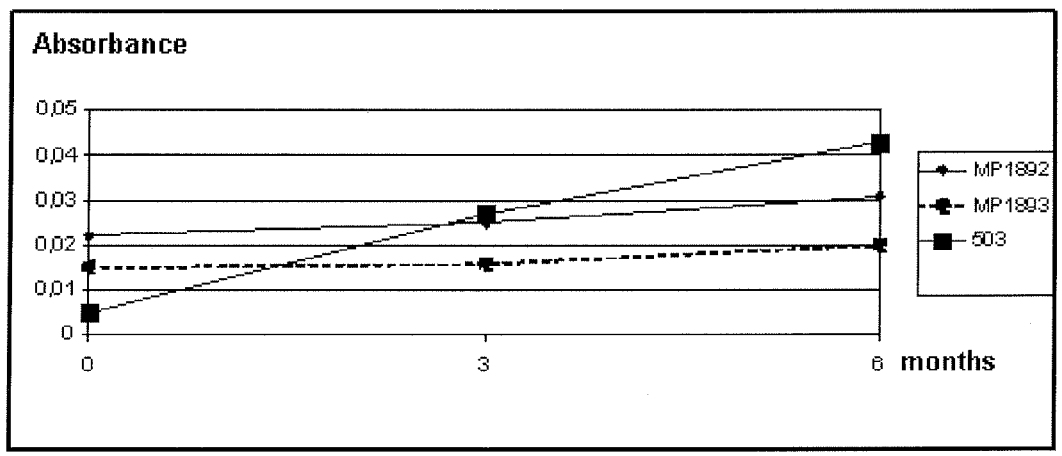
FIG. 1 shows the absorbance of reconstituted formulations MP 1892 and MP 1893 and vinflunine ditatrate starting material (batch No. 503).

Unexpectedly, this invention makes it possible to stabilise hydrosoluble salts of vinflunine and vinorelbine while they are in a pulverulent state. It then becomes possible to store them at room temperature and not below −15° C. as mentioned earlier.

This invention is based on stable formulations of freeze-dried semisynthetic derivatives of vinca alkaloid in the presence of at least one carbohydrate, such as the monosaccharides, reduced or not, oligosaccharides or polysaccharides such as inuline, more particularly on stable formulations of the hydrosoluble salts of semisynthetic derivatives of vinca alkaloid and more particularly still on stable formulations of freeze-dried hydrosoluble salts of vinflunine and vinorelbine in the presence of disaccharides, more specifically saccharose, trehalose or lactose.

The relative proportions of semisynthetic derivatives of vinca alkaloid and carbohydrate can range from 1/1 to 1/20, more specifically from 1/1 to 1/10 (w/w).

Advantageously, the stable formulations of freeze-dried semisynthetic derivatives of vinca alkaloid in the presence of at least one carbohydrate such as the monosaccharides, reduced or not, oligosaccharides or polysaccharides such as inuline, can contain a buffer system with a pH of 3 to 4, more particularly pH=3.5 in order to maintain the pH of the solution obtained after the freeze-dried product is re-dissolved in water for injectable preparations at a value that enhances the good stability of the active ingredient.

As a non-limiting example, these buffer system consist of acetic acid and sodium acetate, citric acid and sodium citrate, tartaric acid and soda. Their molarity is between 0.005 M and 0.5 M and more specifically between 0.05 M and 0.2 M.

The non-toxicity of these starting materials by parenteral route makes it possible to use these freeze-dried products as injectable drugs in the treatment of cancer.

The formulae below, given as non-limiting examples, and their stability results compared to those of the starting material serve to illustrate the invention.

The solutions whose unit composition appears in table 1 below were prepared then freeze-dried.

EXAMPLE 1

TABLE 1

Freeze-dried vinflunine formulations

| Compounds | Formula references | |
|---|---|---|
| | MP1892 | MP1893 |
| Vinflunine ditartrate | 68.35 mg | 68.35 mg |
| corresponding to Vinflunine | 50.00 mg | 50.00 mg |
| Saccharose | 50.00 mg | 75.00 mg |
| Acetic acid/ | qs for 2.00 ml | qs for 2.00 ml |
| sodium acetate buffer 0.1M | | |
| pH = 3.5 | | |

The following manufacturing procedure was applied:
1). successively dissolve with stirring the saccharose and vinflunine ditartrate in the main part of the acetic acid/sodium acetate 0.1 M buffer solution pH=3.5 required for manufacturing,
2). adjust to the final volume with acetic acid/sodium acetate 0.1 M buffer solution pH=3.5 and homogenize the solution obtained,
3). sterilize the solution by filtration on a hydrophilic 0.22 μm polyvinylidene fluoride membrane and distribute into type I glass bottles,
4). Carry out freeze drying operations under the following conditions:
product freezing at −48° C.,
primary desiccation under 0.100 mbar for 37 h at a rate of 0.03° C./min,
secondary desiccation under 0.010 mbar for 16 h at 20° C.
5). stopper the bottles and screw on the caps.

The freeze-dried products obtained were stored for 6 months at 25° C.-60% RH along with one batch of the starting material, vinflunine ditartrate (batch 503).

Figure 2:
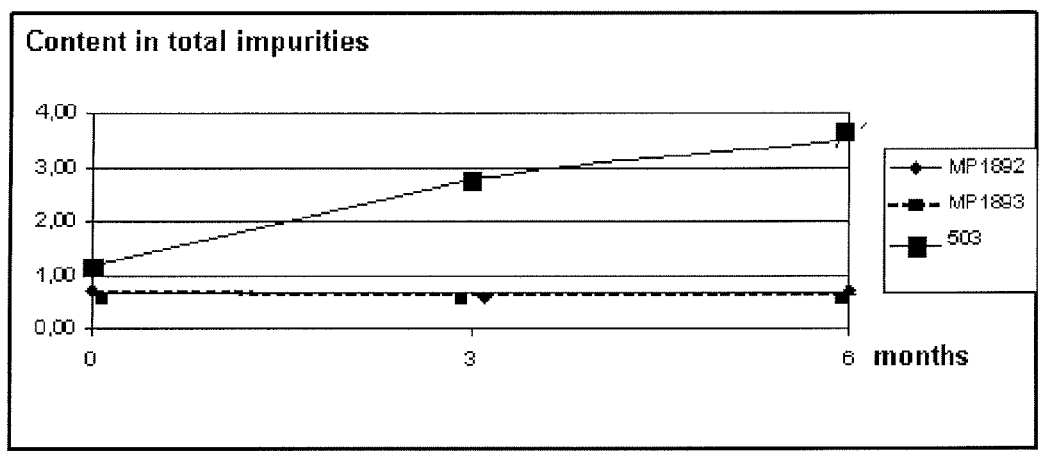
FIG. 2 shows the total impurities of formulations MP 1892 and MP 1893 and vinflunine ditatrate starting material (batch No. 503).

The appearance of impurities, corresponding to the products of degradation, was monitored by recording the changes in:
absorbance at 420 nm of the reconstituted solution, after 6 months at 25° C. and 60% relative humidity, shown in FIG. 1.
total impurities after 6 months at 25° C. and 60% relative humidity, expressed as a percentage, and shown in FIG. 2.

Saccharose has an incontestable stabilizing effect. This effect is all the greater the higher the saccharose content, as seen by the absorbance results at 420 nm.

It should be noted that these totally unexpected excellent results can be further improved. Vinflunine ditartrate is a molecule that is sensitive to oxidation. The person skilled in the art knows very well that combining an inert gas such as nitrogen or argon, or a hydrophilic anti-oxidant agent such as ascorbic acid and its derivatives, the salts of sulphurous acid such as sodium sulphite and thiol derivatives can increase this stability.

The protection conferred on freeze-dried vinflunine by carbohydrates, such as the monosaccharides, reduced or not, oligosaccharides or polysaccharides such as inuline, and more specifically by the disaccharides, is not found with other excipients conventionally used as structuring agents for injectable freeze-dried products.

The compositions below were freeze-dried.

EXAMPLE 2

TABLE 2

Freeze-dried vinflunine formulations

| Compounds | Formula references | |
|---|---|---|
| | MP1762 | MP1766 |
| Vinflunine ditartrate | 68.35 mg | 68.35 mg |
| Corresponding to vinflunine | 50.00 mg | 50.00 mg |
| Trehalose | 80.00 mg | |
| Polyvidone | | 100.00 mg |
| Acetic acid/sodium acetate buffer 0.1M pH = 3.5 | qs for 2.00 ml | qs for 2.00 ml |

The freeze-dried products were stored for 1 month at 5° C., 25° C.-60% RH as well as at 40° C.-75% RH. The last condition was highly a demanding condition in order to amplify the differences found.

Total content in impurities was measured by HPLC and is given as a percentage with respect to vinflunine. The results shown in the table below are the calculated differences between measurements at 25° C.-60% RH, 40° C.-75% RH and those at 5° C.

TABLE 3

Results of total content in impurities relating to vinflunine after 1 month

| | Difference between results at 25° C. and 5° C. | Difference between results at 40° C. and 5° C. |
|---|---|---|
| MP1762 | 0% | 0.5% |
| MP1766 | 0.8% | 2.4% |

The results obtained for formula MP1762 (trehalose) are good and identical at 25° C.-60% RH and 5° C.

The results obtained for formula MP1766 (polyvidone) are clearly not favourable.

All these results, especially those obtained for 6 months of storage at 25° C.-60% RH, come together to make it possible for the formulator to release anti-cancer compositions with a shelf-life of over 18 months at room temperature which eliminates the constraint of having to transport and store the formulations at a temperature between 2° C. and 8° C.

Advantageously, the composition of the invention contains a unit quantity of over 50 mg of vinflunine.

In an advantageous embodiment, the composition of the invention can contain a unit quantity of over 50 mg of vinflunine, for example 100 mg or 250 mg. From this perspective, the formulation of the solution prior to freeze-drying remains the same, only the volume of the distributed solution changes: 4 ml and 10 ml for the previously mentioned doses of 100 mg and 250 mg vinflunine.

The solutions whose unit composition is given in the table below were prepared then freeze-dried.

EXAMPLE 3

TABLE 4

Freeze-dried vinorelbine formulations

| Compounds | Formula references | |
|---|---|---|
| | AD341 | AD344 |
| Vinorelbine ditartrate | 28.52 mg | 28.52 mg |
| corresponding to vinorelbine | 20.00 mg | 20.00 mg |
| Saccharose | 200.00 mg | |
| Inuline | | 200.00 mg |
| Acetic acid/sodium acetate buffer 0.1M pH = 3.5 | qs for 2.00 ml | qs for 2.00 ml |

The freeze-dried products obtained were stored for 1 month at 25° C.-60% RH and 30° C.-65% RH and for 2 months at 5° C. and 25° C.-60% RH.

Total content in impurities was measured by HPLC and is given with respect to the initial value.

TABLE 5

Results of total content in impurities after
1 month with respect to the initial value

| | Difference between results at $T_0$ and 25° C. | Difference between results at $T_0$ and 30° C. |
|---|---|---|
| AD341 | +0.13% | +0.12% |
| AD344 | +0.05% | +0.04% |

TABLE 6

Results of total content in impurities after
2 months with respect to the initial value

| | Difference between results at $T_0$ and 25° C. | Difference between results at $T_0$ and 5° C. |
|---|---|---|
| AD341 | +0.10% | +0.06% |
| AD344 | +0.04% | +0.04% |

Under the same storage conditions, the starting material, vinorelbine ditartrate, shows a change in the level of degradation impurities, which means the product needs to be stored T<−15° C. (average change equal to +0.3% after 3 months at 5° C.).

The results obtained are highly favourable in terms of storage at room temperature of vinorelbine present in ditartrate form and freeze-dried in the presence of a carbohydrate.

The composition according to this invention can also contain a unit quantity below or equal to 20 mg of vinorelbine, for example 10 mg and 50 mg. Formulation of the solution prior to freeze-drying remains exactly the same and only the distribution volume changes: 1 ml and 5 ml for the above-mentioned doses of 10 mg and 50 mg available on the market.

In one particular embodiment of the invention, the pharmaceutical composition according to this invention is administered by infusion by intravenous route after reconstitution in water for injectable preparations and dilution in infusion solutions such as 0.9% sodium chloride or 5% glucose solutions.

This invention also relates to the pharmaceutical composition according to the invention for use as a medication, particularly in the treatment of cancer, advantageously by parenteral administration, in an advantageous manner by intravenous route by infusion, and even more advantageously during chemotherapy as an antineoplasic and antitumoral agent.

This invention also relates to the use of the composition according to the invention for the manufacture of a medication intended for parenteral administration, advantageously by intravenous route by infusion, advantageously for the treatment of cancer.

Parenteral administration, namely by intravenous route, of a pharmaceutical composition of vinflunine or vinorelbine according to this invention makes it possible to treat cancers that are sensitive to the effect of vinflunine or vinorelbine.

The invention claimed is:

1. Pharmaceutical compositions consisting of a hydrosoluble salt of vinflunine or vinorelbine, stable at room temperature, wherein said hydrosoluble salt of vinflunine or vinorelbine is in a freeze-dried form obtained in the presence of at least one carbohydrate, at least one buffer system and a hydrophilic anti-oxidation agent.

2. Compositions according to claim 1 wherein the hydrosoluble salt of vinflunine or vinorelbine is vinflunine ditartrate or vinorelbine ditartrate.

3. Compositions according to claim 1 wherein the carbohydrate (s) is chosen from among the monosaccharides, reduced or not, oligosaccharides or polysaccharides.

4. Compositions according to claim 3 wherein the carbohydrate (s) is chosen from among saccharose, trehalose and lactose.

5. Compositions according to claim 1 wherein the buffer system chosen to control the pH has a value between 3 and 4 and a molarity between 0.005 M and 0.5 M.

6. Compositions according to claim 1 wherein said compositions are manufactured and packaged under an inert gas atmosphere and/or with incorporation of a hydrophilic anti-oxidation agent into the formula.

7. Compositions according to claim 1 wherein said compositions are in a form suited to administration by infusion by intravenous route.

8. Compositions according to claim 3 wherein the carbohydrate (s) is disaccharides.

9. Compositions according to claim 3 wherein the carbohydrate (s) is inuline.

10. Compositions according to claim 5 wherein the buffer system chosen to control the pH has a value in the region of 3.5 and a molarity between 0.05 M and 0.2 M.

11. Pharmaceutical compositions consisting of a hydrosoluble salt of vinflunine or vinorelbine, stable at room temperature, wherein said hydrosoluble salt of vinflunine or vinorelbine is in a freeze-dried form obtained in the presence of at least one carbohydrate.

\* \* \* \* \*